United States Patent
Foucher et al.

(10) Patent No.: US 11,972,595 B2
(45) Date of Patent: Apr. 30, 2024

(54) GAS SENSOR

(71) Applicants: OFFICE NATIONAL D'ETUDES ET DE RECHERCHES AÉROSPATIALES, Palaiseau (FR); TOTAL SA, Courbevoie (FR)

(72) Inventors: Pierre-Yves Foucher, Pechbusque (FR); Guillaume Druart, Palaiseau (FR)

(73) Assignees: OFFICE NATIONAL D'ETUDES ET DE RECHERCHES AÉROSPATIALES, Palaiseau (FR); TOTALENERGIES SE, Courbevoie (FR)

( * ) Notice: Subject to any disclaimer, the term of this patent is extended or adjusted under 35 U.S.C. 154(b) by 394 days.

(21) Appl. No.: 17/601,822

(22) PCT Filed: Apr. 6, 2020

(86) PCT No.: PCT/EP2020/059746
§ 371 (c)(1),
(2) Date: Oct. 6, 2021

(87) PCT Pub. No.: WO2020/207962
PCT Pub. Date: Oct. 15, 2020

(65) Prior Publication Data
US 2022/0215591 A1  Jul. 7, 2022

(30) Foreign Application Priority Data
Apr. 8, 2019  (FR) ....................... 1903745

(51) Int. Cl.
*G06K 9/00* (2022.01)
*G01J 5/00* (2022.01)
(Continued)

(52) U.S. Cl.
CPC .............. *G06T 7/97* (2017.01); *G01J 5/0014* (2013.01); *G01M 3/04* (2013.01); *G01M 3/38* (2013.01);
(Continued)

(58) Field of Classification Search
CPC ........ G01N 21/25; G01N 21/29; G01N 21/31; G01N 21/314; G01N 21/3504;
(Continued)

(56) References Cited

U.S. PATENT DOCUMENTS 5,656,813 A    8/1997  Moore et al.
9,958,328 B2*  5/2018  Cabib ................ G01N 21/3504
(Continued)

FOREIGN PATENT DOCUMENTS

JP   H0599779 A    4/1993
JP   H11503237 A   3/1999
(Continued)

OTHER PUBLICATIONS

Office Action issued in Japanese Patent Application No. 2021-559547 dated Oct. 17, 2023.
(Continued)

*Primary Examiner* — Eric Rush
(74) *Attorney, Agent, or Firm* — NIXON & VANDERHYE

(57) ABSTRACT

A gas detector for revealing a target gas includes an image capturing unit with multiple optical channels, an image processing unit and a calculation unit. The image processing unit is adapted for deducing a value of a radiation transmission coefficient which relates to an analysis spectral band, and which is attributable to a quantity of the target gas present in a part of the field-of-view. Preferably multiple analysis bands are used in parallel. The calculation unit is adapted for deducing an evaluation of the quantity of the
(Continued)

target gas based on the value of the radiation transmission coefficient which relates to each analysis band. Such a gas detector may have small dimensions, be easily transportable, including on board a drone, and can provide evaluation results for the quantity of the target gas in real-time or nearly real-time.

20 Claims, 3 Drawing Sheets

(51) Int. Cl.
| | |
|---|---|
| *G01M 3/04* | (2006.01) |
| *G01M 3/38* | (2006.01) |
| *G01N 21/3504* | (2014.01) |
| *G01N 21/61* | (2006.01) |
| *G06T 7/00* | (2017.01) |

(52) U.S. Cl.
CPC ......... *G01N 21/3504* (2013.01); *G01N 21/61* (2013.01)

(58) Field of Classification Search
CPC ............... G01N 21/3518; G01N 21/61; G01N 33/0027; G01N 33/0031; G01N 2021/1793; G01N 2021/1795; G01N 2021/3155; G01N 2021/3531; G01N 2021/8578; G06T 7/97; G06T 2207/10036; G06V 10/12; G06V 10/143; G06V 10/147; G06V 20/10; G06V 20/13; G06V 20/194; G06V 20/52; G06F 18/20; G01M 3/002; G01M 3/007; G01M 3/04; G01M 3/202; G01M 3/22; G01M 3/38; G01J 3/2823; G01J 3/36; G01J 5/0014; G01J 2003/2826; G01J 2005/0074; G01J 2005/0077; G01J 2005/0092; G08B 21/12; G08B 21/14; G08B 21/16

USPC ....... 382/100, 103, 109, 128, 181, 190, 191, 382/224, 254, 274, 302–304, 312, 325; 356/432, 433, 435–439, 450, 451, 456; 250/252.1, 316.1, 330, 332, 338.1, 338.5, 250/339.01–339.4, 339.11–339.13, 340, 250/343, 357.1, 564, 565; 73/1.02, 1.06, 73/23.2, 23.25, 25.05

See application file for complete search history.

(56) References Cited

U.S. PATENT DOCUMENTS

| | | | |
|---|---|---|---|
| 10,684,216 B2* | 6/2020 | Wang | G01N 21/314 |
| 10,724,919 B2* | 7/2020 | Grimberg | G06T 7/001 |
| 11,573,172 B2* | 2/2023 | Lannestedt | G01N 21/3504 |
| 11,641,441 B2* | 5/2023 | Schmidt | G06T 7/11 348/164 |
| 2010/0018289 A1 | 1/2010 | Oda | |
| 2016/0097713 A1 | 4/2016 | Kester et al. | |
| 2016/0238451 A1 | 8/2016 | Zeng | |
| 2018/0011009 A1 | 1/2018 | Sandsten et al. | |
| 2018/0292291 A1 | 10/2018 | Tsuchiya | |

FOREIGN PATENT DOCUMENTS

| | | |
|---|---|---|
| JP | 2009174990 A | 8/2009 |
| JP | 2013122389 A | 6/2013 |
| WO | 2015/166265 | 11/2015 |
| WO | 2017073426 A1 | 5/2017 |

OTHER PUBLICATIONS

International Search Report and Written Opinion of the ISA for PCT/EP2020/059746, dated Jul. 8, 2020, 13 pages.

\* cited by examiner

GAS SENSOR

This application is the U.S. national phase of International Application No. PCT/EP2020/059746 filed 6 Apr. 2020, which designated the U.S. and claims priority to FR Patent Application No. 1903745 filed 8 Apr. 2019, the entire contents of each of which are hereby incorporated by reference.

FIELD OF THE INVENTION

The invention relates to a gas detector, for example for detecting leaks of a gas such as methane in an arbitrary environment, in particular outdoors.

DESCRIPTION OF RELATED ART

Many situations require determining whether an identified gas is present in a space zone, whether in an outdoor environment or inside a closed volume, for example, in a building or a mine. This may be for confirming safety of a site which could contain quantities of a dangerous or toxic gas, or for searching for the occurrence of an accidental leak in a pipeline used for carrying or distributing gas. In particular, such detection needs relate to facilities for routing and distributing methane ($CH_4$), but such needs also exist for other gases depending upon the applications involved.

A well-known manner for detecting gases consists in using an imaging instrument which is sensitive to radiation in a spectral band where the gas is absorbing. Documents US 2016/097713 and US 2018/011009 provide descriptions of such imaging instrument. In general, it involves an infrared band for which the atmosphere is at least partially transparent, and images of one and same scene are captured repetitively. When a release of gas occurs in the scene, such that a distribution of the gas varies inside the field-of-view of the imaging instrument, the images which are successively captured contain areas where the scene is at least partially obscured by the gas, and the limits of these areas vary between successive images. These variations then serve to confirm the presence of the gas, on the condition that the scene which is imaged in background is static.

However, such detection method in general produces a high rate of false alarms. These false alarms may be due in particular to the background of the captured images, where contributions thereof to these images are incorrectly attributed to the gas being sought. For example, such contributions may result from direct and variable solar lighting onto elements of the scene which are present in the background.

TECHNICAL PROBLEM

From this situation, an object of the present invention is to provide a new method of detection for a gas which has a reduced rate of false alarms. In particular, such method is desired which serves to more efficiently detect the gas sought with respect to scene elements present in the background, as such scene elements may exist in various environments, outdoors or inside.

Another object of the invention is to have a quantitative method for detecting the gas, which allows to evaluate a quantity of the gas present in a space zone, instead of a method limited to evaluating temporal variations of this quantity.

A further object is to propose such method for detecting the gas which could be easily implemented on-site, meaning in the area where the presence of gas is suspected. In particular, an object of the invention is to propose a gas detector which is not heavy and not bulky, in particular in order to be easily carried or installed on board a drone.

Finally, another object of the invention is to propose a method for detecting the gas which provides a quantitative evaluation result in real-time or nearly real-time.

BRIEF SUMMARY OF THE INVENTION

In order to achieve at least one of these objects or another, the invention proposes a new gas detector for revealing at least one gas which is called target gas and which could be present in a field-of-view. This gas detector comprises:
  an image capturing unit, which comprises at least two optical channels arranged in parallel for separately and simultaneously capturing respective images of one and same content of the field-of-view, called spectral images, in different spectral bands to which said channels are dedicated one-to-one;
  first acquisition means adapted for providing an ambient temperature value, intended to be attributed to a quantity of the target gas which is present in the field-of-view between a background scene and the image capturing unit;
  second acquisition means, adapted for providing, for at least one of the spectral bands called analysis band, background brightness temperature values which are intended to be attributed to elements of the background scene;
  an image processing unit, arranged for receiving the spectral images captured by each channel of the image capturing unit, and adapted for deducing, separately for each analysis band, and evaluation of a radiation transmission coefficient which relates to this analysis band, and which is attributed at least partially to a quantity of the target gas present in a part of the field-of-view between the background scene elements and the image capturing unit, based on an equation which combines:
    the ambient temperature value;
    the background brightness temperature value attributed to the background scene elements in the relevant part of the field-of-view, for the relevant analysis band; and
    at least one brightness temperature value, called apparent brightness temperature value, which corresponds to the spectral image captured for the analysis band, in the part of concern of the field-of-view; and
  a calculation unit, adapted for deducing an evaluation of the quantity of target gas which is present in the field-of-view, based on the value of the radiation transmission coefficient which relates to the analysis band.

In particular, the part of the field-of-view for which the quantity of target gas present is evaluated may correspond to an image point (pixel) of the spectral image which was captured for this analysis band. Alternatively, it may correspond to a binning of several image points, which may be adjacent to each other.

According to the invention, the first acquisition means are adapted for providing the ambient temperature value in one of the following ways:
  based on at least one part of a spectral image which was captured by one of the image capturing unit input channels, where this spectral image part corresponds to a sector of the field-of-view declared or considered as being free of background scene elements; and
  based on at least one part of a spectral image which was captured by one of the channels of the image capturing unit, whose associated spectral band is contained in a spectral domain of complete opacity of a gas which is present in a sector of the field-of-view corresponding to the spectral image portion.

In that way, with the invention, it is not necessary that the gas detector incorporates an additional temperature sensor, in particular a temperature sensor which makes a thermal measurement. The gas detector design is simplified that way. Furthermore, since the ambient temperature value is obtained in a way similar to that of each analysis band brightness temperature value, a better agreement of values results, which improves the reliability and precision of the target gas detection.

According to an additional feature of the invention, the gas detector is adapted for capturing the spectral image at least a part of which is used for providing the ambient temperature value, at the same time or during a single image capturing sequence as the spectral image of each analysis band, when the image processing unit next combines this ambient temperature value with at least one brightness temperature value of the spectral image of analysis band. Thus, each operation sequence of the gas detector may be sufficient and autonomous for providing an evaluation of the quantity of the target gas which is present in the part of the field-of-view, without requiring using one or more spectral images captured earlier. Memory capacity of the gas detector can be reduced in that way, and a time consistency is ensured between respective contents of spectral images which are combined in order to get a target gas quantity evaluation.

In various embodiments of the invention, the image capturing unit may comprise for example two, four, six, nine, twelve or sixteen optical channels which are arranged in parallel, without limitation but preferably at most twenty channels.

An equation which may be used by the image processing unit for evaluating the transmission coefficient of the radiation which relates to the analysis band, and which is attributed at least partially to the target gas, may have the form:

$$\tau_{band\_1} = 1 + (TB_{apparent\_1} - TB_{background\_1}) / (TB_{background\_1} - T_{ambient}),$$

where $\tau_{band\_1}$ is the value of the transmission coefficient for the radiation which relates to the analysis band, indicated by band_1, and which is attributed at least partially to the target gas present in the part of the field-of-view;

$T_{ambient}$ is the ambient temperature value which is provided by the first acquisition means;

$TB_{background\_1}$ is the background brightness temperature value, which is provided by the second acquisition means, and which is attributed to the background scene elements contained in the part of the field-of-view, for the analysis band band_1; and $TB_{apparent\_1}$ is the apparent brightness temperature value, which corresponds to the spectral image captured for the analysis band band_1, in the part of the field-of-view.

Such an equation is simple and quick to implement, and compatible with obtaining a quantitative detection result for the target gas in real-time or nearly real-time. When the resulting value for the transmission coefficient $\tau_{band\_1}$ is not contained between 0 and 1, these two limits being accepted, the result may be set aside. Such an inconsistency may have been caused by a change of the background between one moment at which the background brightness temperature was determined and the moment of acquisition of the spectral image used for determining the apparent brightness temperature. It may also have been caused by a change in the ambient temperature between one moment at which this ambient temperature was determined and the moment of acquisition of the spectral image used for determining the apparent brightness temperature. Yet another reason may be the presence of another gas in the part of the field-of-view, which contributed to the brilliance captured in the spectral image or which has been involved in the operation of the first and/or second acquisition means. These causes of inconsistency could be reduced by using first and second acquisition means which produce data relative to the same moment as that of the capturing of each analysis band spectral image.

Advantageously, when the gas detector comprises several analysis bands, the preceding equation for evaluating the transmission coefficient of the radiation may be used separately for each of these analysis bands, in order to evaluate the transmission coefficient for the radiation which relates to that analysis band independently of each other analysis band. The use of multiple analysis bands serves, generally for the invention, to get a more reliable evaluation of the quantity of the target gas.

Preferably, the image processing unit may further be adapted for applying to each spectral image a correction of luminance values as captured by the image capturing unit, in order to take into account at least one atmospheric compound which is present in the field-of-view. The corrected luminance values are then used by the image processing unit for evaluating the transmission coefficient of the radiation relating to each analysis band. The atmospheric compound which may be taken into consideration that way may be water vapor, and/or possibly carbon dioxide.

The calculation unit may be adapted for determining the quantity of the target gas which is present in the part of the field-of-view, referenced as $Q_{target\ gas}$, by inverting an equation which connects the value of the radiation transmission coefficient to that quantity of the target gas, for each analysis band. Indeed, in a simplified case of uniform distribution of the target gas within a plume, the equation may be of the type: $\tau_{band\_1} = \exp(-Q_{target\ gas} \cdot Abs_{band\_1})$, where $Abs_{band\_1}$ is the absorbance of the target gas in the analysis band band_1. However, a more precise calculation can be performed in order to consider more complex variations of the target gas concentration in the plume. It is then preferable to have for each analysis band, a table of values for the radiation transmission coefficient as a function of the profiles of the concentration of the target gas along the radiation path which connects a background scene element to the image capturing unit. To this end, the calculation unit may advantageously be arranged for determining the quantity of the target gas which is present in the part of the field-of-view by comparing the values of the radiation transmission coefficients which were deduced by the image processing unit separately for multiple analysis bands, with values of these radiation transmission coefficients which were predetermined for the same analysis bands. Errors which could affect the digital results obtained for the target gas concentration can be reduced in this way. The predetermined values for the radiation transmission coefficients, which could be obtained by prior calculations, may then be recorded in a data storage unit which is accessible to the calculation unit. They relate to variable profiles of the concentration of the target gas on the radiation path which connects a background scene element to the image capturing unit. The value of the quantity of target gas then corresponds to a spatial integration of the concentration profile of the target gas over the radiation path between the background scene element and the image capturing unit. Such use of predetermined values, in the form of a table indexed as a function of the concentration profiles of the target gas, makes it possible to reduce calculations to be performed during each target gas detection session. In this way, the quantitative target gas detection result may be obtained in real-time or nearly real-time, for each detection sequence which is carried out.

Preferably, the spectral bands of the channels of the image capturing unit may be such that the target gas has absorption values which are different between two different spectral bands. Alternatively or in combination, the spectral bands of the channels of the image capturing unit may be such that the target gas has values of a quotient which are different between two different spectral bands, where the quotient is calculated for each spectral band as the absorption value of the target gas in that spectral band, divided by the absorption value of at least one atmospheric component present in the field-of-view, in the same spectral band.

When the ambient temperature value is provided by the first acquisition means based on a spectral image portion which corresponds to a sector of the field-of-view declared or considered to be free of background scene elements, the image capturing unit may be oriented in order to take this spectral image such that the sector of the field-of-view is at least partially occupied by a sky zone, without intermediate scene element between the sky zone and the image capturing unit.

Generally, the ambient temperature value may correspond to a brightness temperature value of an atmospheric compound which is deduced from the spectral image part of concern for the spectral band of the channel used.

The second acquisition means may be adapted for providing the background brightness temperature values according to one of the following ways:

from at least one spectral image which contains one of the background scene elements, which was captured by the channel of the image capturing unit dedicated to the analysis band, and which is declared or considered as having been captured when the field-of-view did not contain target gas;

from at least one spectral image which contains one of the background scene elements, which was captured by one of the channels of the image capturing unit for which the corresponding spectral band, called reference band, is contained in a spectral domain of transparency of the target gas, or in which transparency band the target gas has a transparency greater than in each analysis band, the image processing unit being adapted for identifying a material of the background scene element from the spectral image captured for the reference band, and for deducing the background brightness temperature value for each analysis band and for the background scene element, based on the ambient temperature value and a spectral emissivity value of the identified material for said background scene element; and from at least one spectral image which contains one of the background scene elements, which was captured by one of the channels of the image capturing unit for which the corresponding spectral band, called reference band, is contained in a spectral domain of transparency of the target gas, or in which transparency band the target gas has a transparency greater than in each analysis band, the image processing unit being adapted for producing the background brightness temperature values for each analysis band by using a linear regression based on background brightness temperature values deduced from the spectral image captured for the reference band. According to an improvement, several linear regressions may be implemented separately inside decomposition zones common to the spectral images. These decomposition zones may be defined based on the spectral image which was captured for the reference band, and they are such that the brightness temperature values in this spectral image vary in a limited extent inside each decomposition zone.

Advantageously, when the second acquisition means are further adapted for providing the background brightness temperature values based on at least one spectral image captured by a channel of the image capturing unit which corresponds to a reference band, the gas detector may be adapted for capturing the spectral image which corresponds to this reference band in the same time or during the same image capturing sequence as the spectral image of each analysis band. In that way, the following advantages of the invention are additionally increased:

each operation sequence of the gas detector is sufficient and autonomous for providing an evaluation of the quantity of the target gas, without requiring one or more spectral images captured earlier;

the memory capacities of the gas detector may be reduced; and a time consistency is ensured between respective contents of spectral images which are combined in order to get a target gas quantity evaluation.

In preferred embodiments of the invention, the image capturing unit may comprise a matrix image sensor which is common to all the channels, and which is simultaneously sensitive in all the spectral bands of these channels. Then, a part of a photosensitive surface of this image sensor may be dedicated to each channel, separately from each other channel. Then, each channel comprises, inside the image capturing unit:

an optical part which is arranged in order to form an image of a content of the field-of-view on the part of the photosensitive surface dedicated to this channel, where the field-of-view is common to all the channels; and spectral filtering means, which are adapted for determining the spectral band of the channel.

With such an optical configuration, the image capturing unit can be implemented in the form of a single module, particularly compact and reduced in weight. The gas detector can then be portable, and/or easily mounted on board a drone. The possibility of use on board a drone is particularly advantageous when the gas to be detected is dangerous, in particular when it is toxic.

The image sensor may be quantum sensor type and, optionally, the gas detector may further comprise cooling means which are arranged for cooling the image sensor to a temperature below 150 K (Kelvin).

Generally for the invention, each channel of the image capturing unit may comprise spectral filtering means such that the spectral band of this channel has a width which is comprised between 10 nm (nanometer) and 500 nm (or 0.50 µm), in terms of wavelength of the radiation. These spectral filtering means may then be adapted so that the spectral bands of the channels are contained in a first spectral domain which corresponds to radiation wavelengths comprised between 7 µm and 10 µm. This first spectral domain is commonly designated by LWIR, for "long wavelength infrared." Alternatively, the spectral filtering means may be adapted so that the spectral bands of the channels are contained in a second spectral domain which corresponds to radiation wavelengths comprised between 3 µm and 5 µm.

This second spectral domain is commonly designated by MWIR, for "mid-wavelength infrared."

For a gas detector which conforms to the invention, adapted for methane as the target gas, and which is operational in the LWIR range:
- the spectral band of a first of the channels may extend around 7.7 µm, with a spectral bandwidth which is less than 0.35 µm;
- the spectral band of a second of the channels may extend around 8.05 µm, with a spectral bandwidth which is less than 0.35 µm;
- the spectral band of a third of the channels, optional, may extend around 7.35 µm, with a spectral bandwidth which is less than 0.35 µm; and
- the spectral band of a fourth of the channels, also optional, may extend around 8.35 µm or 9.05 µm, with a spectral bandwidth which is less than 0.35 µm.

For another gas detector which conforms to the invention, also adapted for methane as the target gas, but which is operational in the MWIR range:
- the spectral band of a first of the channels may extend around 3.375 µm, with a spectral bandwidth which is less than 0.30 µm;
- the spectral band of a second of the channels may extend around 3.225 µm, with a spectral bandwidth which is less than 0.30 µm;
- the spectral band of a third of the channels, optional, may extend around 3.05 µm, with a spectral bandwidth which is less than 0.30 µm; and
- the spectral band of a fourth of the channels, also optional, may extend around 4.237 µm or 3.505 µm, with a spectral bandwidth which is less than 0.30 µm.

In some cases, it may be difficult to arrange a bandpass filter in order to produce the spectral band of at least one of the optical channels for the image capturing unit. Then, it is possible to make this optical channel in the form of a composite optical channel, based on two of the optical channels of the image capturing unit which are in this case called base optical channels. The spectral band of the composite optical channel then results from the relative positions and spectral bandwidths of the respective spectral bands of these two base optical channels. The spectral filter of each base optical channel may be of bandpass type, in particular with a spectral position and/or a spectral bandwidth which is (are) different from that (those) of the spectral band of the composite optical channel, or be of high-pass or low-pass type. Then, the gas detector, in particular the image acquisition and processing units, may be adapted for combining the spectral images which are captured separately by the two base optical channels for one and content of the field-of-view, in order to get a spectral image which corresponds to the spectral band of the composite optical channel. In particular, the gas detector may be adapted for calculating a difference between the spectral images which are captured by the two base optical channels for the same content of the field-of-view, in order to get the spectral image which corresponds to the spectral band of the composite optical channel.

Finally, generally, a gas detector conforming to the invention may be adapted for revealing several different target gases which could be simultaneously present in the same field-of-view. In this case, the spectral band of at least one channel of the image capturing unit may be simultaneously contained in respective spectral absorption domains of at least two of the target gases. In that way, one same spectral image which is captured by this channel may be used by the image processing unit and the calculation unit for deducing evaluations of respective quantities of these at least two target gases which are present in the field-of-view. In other words, the same spectral band from the image capturing unit may serve as analysis band for said at least two target gases.

BRIEF DESCRIPTION OF THE DRAWINGS

The features and advantages of the present invention will appear more clearly in the following detailed description of non-limiting examples of implementation, referring to the attached figures among which.

DETAILED DESCRIPTION OF THE INVENTION

For reasons of clarity, the dimensions of the elements which are shown in these figures do not correspond either to actual dimensions, or to actual dimension ratios. Further, identical references which are indicated in the various figures designate elements which are identical or which have identical functions.

In the remainder, the invention is described in detail for a gas detector with four optical channels, and for a gas detector which is designed for revealing the presence of gaseous methane in a terrestrial environment. The spectral bands are then selected not only as a function of the target gas to be detected, i.e. methane, but also depending on the absorption bands of the compounds of the terrestrial atmosphere. Among the compounds of the atmosphere which need to be considered, water vapor ($H_2O$) is particularly important, but carbon dioxide ($CO_2$) may also be involved in the analysis method which is implemented in the detector. However, it is understood that the invention is not limited to methane as target gas, that a different number of optical channels may be used, where this number of channels is greater than or equal to two and preferably less than nine, and that the detector may be adapted for other environments than terrestrial environments.

Figure 1:
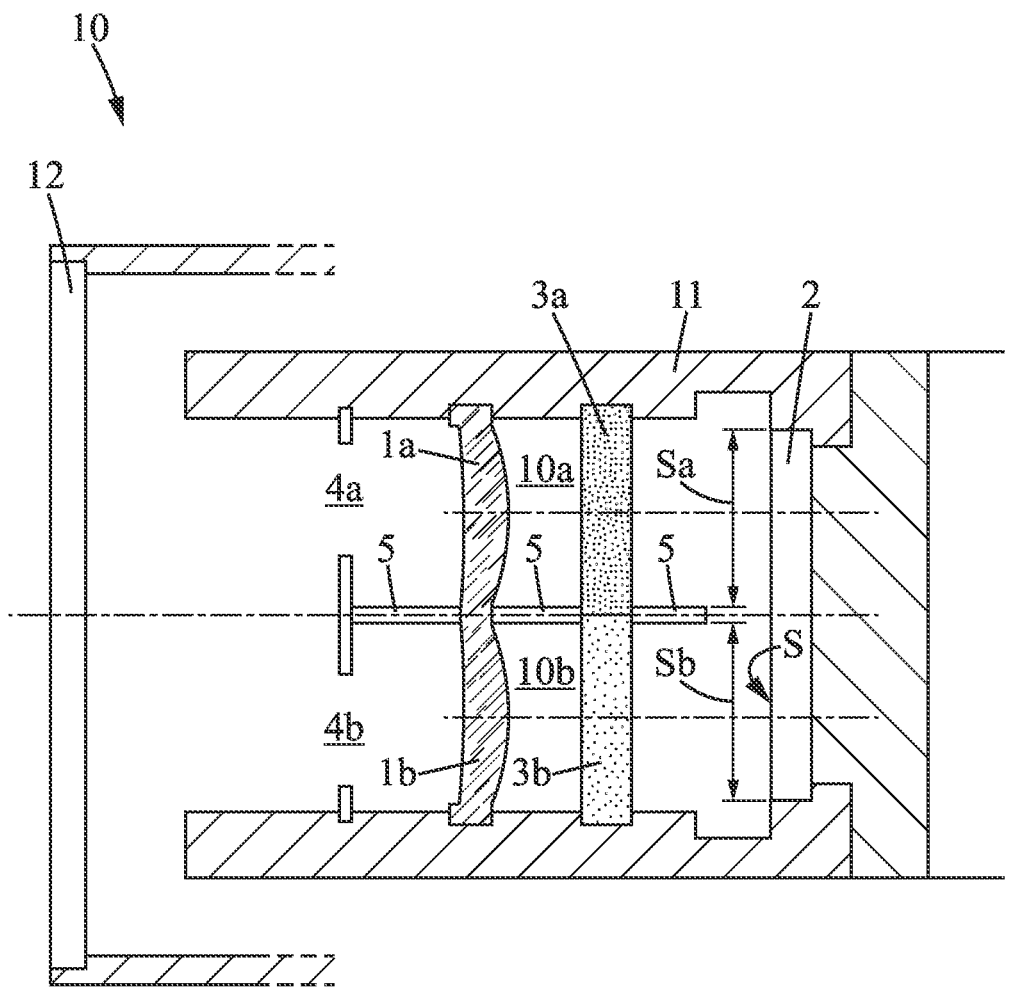
FIG. 1 is a sectional view of an image capturing unit which is part of a gas detector conforming to the invention.

In accordance with to FIG. 1, an image capturing unit 10 may comprise an image formation optics and an image sensor 2 which are assembled inside a single module. For example, a sidewall 11 may hold a 2×2 matrix of four juxtaposed lenses. Two of these lenses, which can be seen in the figure, are referenced 1a, 1b. All the lenses are located at a fixed distance in front of the photosensitive surface S of the image sensor 2. The lenses 1a, 1b, . . . each defines a separate optical channel, by forming respective images of the content of one and same field-of-view on disjoint parts of the photosensitive surface S of the image sensor 2. The references 10a and 10b designate the two optical channels which are visible in the figure, and the references Sa and Sb designate the corresponding parts of the photosensitive surface S of the image sensor 2. Each optical path 10a, 10b, . . . further comprises a spectral filter 3a, 3b, . . . , respectively, which may be located between the lens of the relevant optical channel and the image sensor 2. At least one of the optical surfaces of the lens 1a, 1b . . . of at least one of the optical channels 10a, 10b, . . . could be adapted according to the transmission spectral band of the filter 3a, 3b, . . . of this channel. For the configuration of the image capturing unit 10 which is shown, the distance between each lens 1a, 1b, . . . and the image sensor 2 corresponds to the focal length value shared by all the channels. In that way, the four optical channels 10a, 10b, . . . simultaneously form four separated images of the same content of the field-of-view, but for different spectral bands, as determined by the filters 3a, 3b, . . . . These separate images are called spectral images in the present description. A matrix of aperture diaphragms 4a, 4b, etc. may further be used for adjusting some of the intensity levels of the spectral images produced by the four channels 10a, 10b, . . . relative to others. Further, opaque separators 5 may be arranged between the channels 10a, 10b, . . . for eliminating parasitic rays which could pass between different channels.

As an example, the following numeric values may be adopted for each optical channel of the image capturing unit 10:
focal length of the lenses: 7 mm (millimeter) approximately,
aperture number: 3.9 approximately,
pitch of the photodetectors (pixels) in the photosensitive surface S of the image sensor 2: 15 μm (micrometer), and
field-of-view: 40° (degrees)×30°.
These values correspond to an angular resolution, commonly designated by IFOV for "instantaneous field-of-view", of 0.12°, or 2.1 milliradians. The focal length value, in particular, is compatible with external dimensions of the image capturing unit 10 which are reduced.

The image sensor 2 may be matrix quantum sensor type, for example of HgCdTe technology designated by MCT for Mercury-Cadmium Telluride, which is sensitive to all the transmission spectral bands of the filters 3a, 3b, . . . . In that way, for each operation sequence of the image sensor 2, it outputs data of four spectral images of the content of the field-of-view, respectively for the spectral bands of the four channels 10a, 10b, . . . . For example, the four spectral bands may belong to the LWIR domain or belong to the MWIR domain. In the case of the LWIR domain, but possibly also for the MWIR domain, the image capturing unit 10 may be associated with a cooling system, in order to reduce thermal radiation emitted by the component materials of this image capturing unit, and also to reduce photonic noise from the image sensor 2 and instrumental background noise. The operating temperature of the image capturing unit 10 may then be less than 150 K. When such a cooling system is used, the image capturing unit 10 is contained in a vacuum enclosure, commonly called cryostat, which is thermally coupled to a cooling machine. Reference number 12 designates a transparent window which may be arranged in front of the optical entry of the image capturing unit 10. This window 12 provides an optical aperture for radiation to enter into the image capturing unit 10 while providing a seal for the cryostat.

For methane as the target gas, and for detection in the LWIR spectra domain, a possible choice for the spectral bands for the four optical channels of the image capturing unit 10 may be:
for the spectral band band_1: centered at 7.75 μm with a spectral bandwidth which may be equal to 0.30 μm;
for the spectral band band_2: centered at 8.05 μm with a spectral bandwidth which may be equal to 0.30 μm;
for the spectral band band_3: centered at 7.35 μm with a spectral bandwidth which may be equal to 0.30 μm;
for the spectral band band_4: centered at 8.35 μm or 9.05 μm with a spectral bandwidth which may be equal to 0.30 μm;
These spectral values are understood in terms of wavelength, as all the spectral values which are given in the present description. The spectral band band_1 so-defined is very sensitive to the presence of methane, corresponding to an important absorption domain for this gas. However, it is also very sensitive to the presence of water vapor in the atmospheric composition. The spectral band band_2 is also sensitive to methane and water vapor, although in lesser extents than those of spectral band band_1. The spectral band band_3 is very few sensitive to methane and can be used by the acquisition means 21 which is described below. Finally, the spectral band band_4 is especially sensitive to thermal radiation emitted by all of the scene elements, including those which are present in the background. It can therefore be used by the acquisition means 22 which are also described later.

Another selection of spectral bands which is also possible for methane as the target gas, but for detection in the MWIR spectral domain could be:
for the spectral band band_1: centered at 3.375 μm with a spectral bandwidth which may be equal to 0.20 μm;
for the spectral band band_2: centered at 3.225 μm with a spectral bandwidth which may be equal to 0.20 μm;
for the spectral band band_3: centered at 3.05 μm with a spectral bandwidth which may be equal to 0.20 μm;
for the spectral band band_4: centered at 4.237 μm or 3.505 μm with a spectral bandwidth which may be equal to 0.20 μm;
In this other selection, the spectral band band_1 is very sensitive to the presence of methane, corresponding again to an important absorption domain for this gas. An advantage of this spectral band is to be sensitive in a reduced extent to water vapor which is present in the atmospheric composition. However, it is generally very sensitive to a direct incidence of a solar flux on the elements of the background scene. The spectral band band_2 is also sensitive to methane, although to a lesser extent than that of spectral band band_1. It is more sensitive to the presence of water vapor than the spectral band band_1, but less sensitive to the incidence of direct solar flux, again in comparison with spectral band_1. The spectral band band_3 is not much sensitive to the presence of methane, but very sensitive to the presence of water vapor. It can then be used by the acquisition means. Finally, the spectral band band_4 is very few sensitive to methane at 4.237 μm and at 3.505 μm. At 4.237 μm it is especially sensitive to carbon dioxide present in the atmospheric composition and may also be used by the acquisition means 21. At 3.505 μm, the spectral band band_4 is especially sensitive to background scene elements, and may be used by the acquisition means 22.

Figure 2:
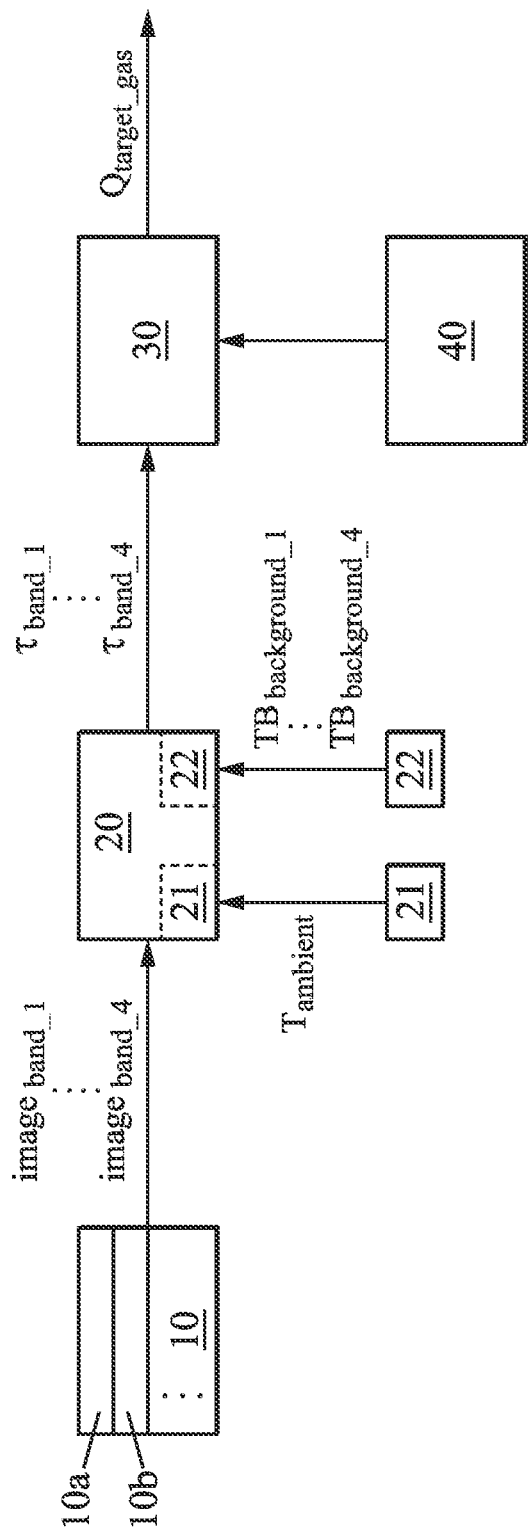
FIG. 2 is an overview drawing of various elements of a gas detector conforming to the invention.

In accordance with FIG. 2, the gas detector comprises the image capturing unit 10, an image processing unit 20 and a calculation unit 30 which are connected to each other to allow the following data transfers:
from the image capturing unit 10 to the image processing unit 20: images which are captured simultaneously in the different spectral bands, noted $image_{band\_1}$, . . . , $image_{band\_4}$ in the case of FIG. 1 where the image capturing unit has four optical channels, band_1, . . . band_4 designating again the four spectral bands. In that way, $image_{band\_1}$ has been captured by filtering the radiation according to spectral band band_1, for example by the optical channel 10a, . . . , $image_{band\_4}$ has been captured by filtering the radiation according to spectral band band_4, by one of the optical channels other than that of $image_{band\_1}$;
from the image processing unit 20 to the calculation unit 30: values of radiation transmission coefficients, noted $\tau_{band\_1}$, . . . , $\tau_{band\_4}$, relating separately to the spectral bands band_1, . . . band_4. Each value for one of the transmission coefficients further relates to one identified part within the field-of-view of the image capturing unit 10. For example, a value of each transmission coefficient $\tau_{band\_1}, \ldots, \tau_{band\_4}$ is determined separately for each image point, or pixel, of each spectral image $image_{band\_1}, \ldots, image_{band\_4}$; and at the output of the calculation unit 30: a value $Q_{target\_gas}$ of the quantity of the target gas which is contained in each identified part of the field-of-view.

Reference number 21 denotes means for getting and transmitting an ambient temperature value $T_{ambient}$ to the image processing unit 20. This value, $T_{ambient}$, relates to the gaseous atmosphere which is present in the field-of-view of the image capturing unit 10, and also relates to the target gas which may be present there. Indeed, target gas which may originate from a point source with a different temperature very quickly comes to thermal equilibrium with the surrounding atmosphere. The target gas therefore essentially has the temperature value $T_{ambient}$ inside the field-of-view, except possibly in an area very close to the point source thereof, which is negligible most times compared to the target gas plume volume already emerged.

The means 21 which provide the value $T_{ambient}$ of the ambient temperature were called first acquisition means in the general part of the present description. They could be made up, in principle, of a thermal temperature sensor which would be in contact with the atmosphere, such as a thermometer. In such a case, which does not correspond to the present invention, the means 21 would be external to the image processing unit 20, connected thereto for transmitting the value $T_{ambient}$.

In the invention, the value $T_{ambient}$ is deduced according to Planck's law, based on the radiation intensity which is detected in a spectral image such as captured by one of the optical channels 10*a*, 10*b*, . . . of the image capturing unit 10. To this purpose, it may be necessary to know the materials of the scene elements which are contained in the field-of-view, in order to have the emissivity values thereof. Two situations allow to optically determine the value $T_{ambient}$, by using a function reciprocal with respect to the temperature, of the Planck emission law $B(\lambda, T)$, where $\lambda$ is the wavelength of the radiation detected, T is the temperature of the material which emitted the radiation, and B is the detected brightness value. The first situation is that of a sector of the field-of-view which is turned towards an area of clear sky, for which the thermal emission behavior of the atmosphere is well known. In particular, no quantity of target gas is present in it, or else the spectral band used is insensitive to the target gas. The second situation is that of a sector of the field-of-view which is occupied by a known gaseous composition, where this composition is completely opaque for the spectral band used. Then scene elements which could be present in the background do not contribute to the radiation which is detected by the image capturing unit 10 for this spectral band. The gas composition must then be known, in order to have the emissivity values thereof. Such is the case in a sector of the field-of-view where the gas composition is without target gas, and therefore corresponds to the atmospheric composition. For such embodiments which conform to the invention, where the value $T_{ambient}$ is deduced from spectral images captured by the unit 10, the first means of acquisition 21 may be internal to the image processing unit 20.

Reference number 22 denotes means for getting and transmitting to the image processing unit 20, brightness temperature values of a background which is contained in the field-of-view, for each of the spectral bands. These means 22 were called second acquisition means in the general part of the present description. In possible embodiments of the invention, for which the background composition is initially known, the brightness temperature values of this background can be deduced, by using the Planck emission law, from the ambient temperature value and from relative emissivity values relating to various background elements. To do so, the surfaces of these background scene elements must be in thermal equilibrium with the atmosphere. In particular, the scene elements must not be heat sources nor receive direct solar flux. Such embodiments of the acquisition means 22 are particularly suited when the gas detector is fixedly installed to monitor an area for which the scene elements are unlikely to change substantially on the scale of several tens of seconds, apart from a possible appearance of a quantity of target gas.

In other possible embodiments of the invention, the background brightness temperature values for each spectral band may be deduced from spectral images which were captured by the unit 10 at a moment when no quantity of target gas was present in the field-of-view of the image capturing unit 10. For such other embodiments of the invention, the acquisition means 22 may be internal to the image processing unit 20. Such background brightness temperature values are relative to each spectral band separately, and also relative separately to various background parts such as contained in the field-of-view. For example, $TB_{background\_1}(i, j)$ denotes the background brightness temperature at the image coordinate point (i, j) for a spectral image captured in the spectral band band_1. The notations $TB_{background\_2}(i, j), \ldots, TB_{background\_4}(i, j)$ which are used in the following have identical meanings, respectively for the spectral bands band_2, . . . , band_4.

However, under some circumstances of use of a gas detector conforming to the invention, it is not possible to have spectral images for which the field-of-view is free of target gas. Such is the situation when it involves an ongoing gas leak which started before the gas detector has been brought on-site to confirm the existence of the leak. Several methods are then possible for remedying such an absence of values $TB_{background\_2}(i, j), \ldots, TB_{background\_4}(i, j)$ which are exact.

According to a first one of these methods, one of the spectral bands of the gas detector, called reference band, may be selected for corresponding to a domain of total or nearly total transparency of the target gas and of the atmosphere. Then, the spectral image which is captured for this reference band allows the image processing unit 20 to determine the brightness temperature values which relate to the background scene elements. If each background scene element is recognized, for example by performing a detection of the shape thereof as visible in the spectral image and then by carrying out a shape recognition, the material thereof can be identified. It is then possible to determine its thermodynamic temperature value from its luminance in the reference band, and then the brightness temperature value thereof for any other spectral band, in particular the analysis bands, based on spectral variations of its emissivity function. Each analysis band is intended to be used thereafter for quantitatively evaluating the quantity of target gas which is present in a part of the field-of-view. In principle, each analysis band has been selected such that the target gas has, in that analysis band, a radiation absorbance value which is significant. By extension of this principle, the same method for determining background brightness temperature values may be applied between two spectral bands for which the target gas has absorbance values which are different: that one of the two spectral bands in which the absorbance of the target gas is weakest may be used as a reference band, and the other spectral band in which the absorbance of target gas is higher, may be used as an analysis band.

The following may be another possible method for remedying the absence of values $TB_{background\_2}(i, j), \ldots TB_{background\_4}(i, j)$ which are exact. The brightness temperature values of the spectral image which has been captured for the reference band may be distributed in some preset and disjoint intervals, for example five intervals. Then, zones are identified in the reference band spectral image, for each of these intervals, such that in each zone the brightness temperature values are contained in this interval. An image decomposition thus results, which is transposed in each spectral image captured in an analysis band. Next, separately in each decomposition zone, coefficients can be determined for a linear regression which connects the brightness temperature values in the spectral image of the reference band to those in the spectral image of the analysis band for the same decomposition zone. This linear regression may then be used, for each of the image points inside the corresponding decomposition zone, in order to convert each brightness temperature value in the spectral image of the reference band into a background brightness temperature value for the analysis band, i.e. $TB_{background\_1}(i, j)$ if the considered analysis band is band_1. Such another method does not require implementing a shape recognition process, nor storing emissivity values of materials possible for the background scene elements. In fact, the distinction between the various background scene elements which is provided by the shape analysis in the preceding method is replaced empirically by the classification of the brightness temperature values for the reference band in disjoint intervals. But, this another method is only reliable if the target gas plume occupies a not-important part of each of the decomposition zones. Put another way, the plume appears to be small in each spectral image compared to the background scene elements.

Reference number 40 in FIG. 2 denotes an optional data storage unit, in which the calculation unit 30 can read digital values. The storage unit 40 may be made up by any memory or data writing medium. The use of such a data storage unit is described later.

Figure 3:
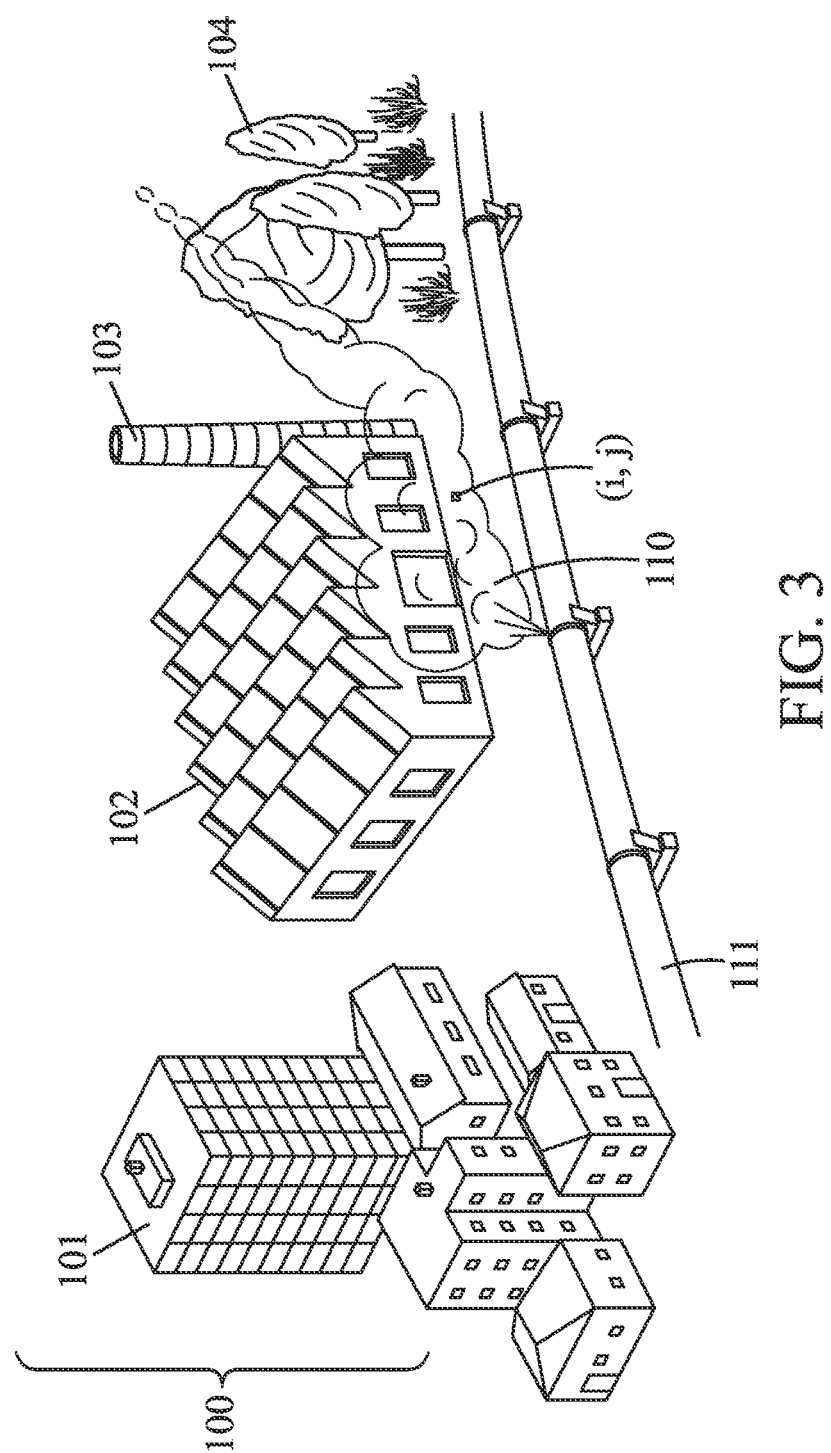
FIG. 3 shows a possible use of a gas detector conforming to the invention.

FIG. 3 shows possible circumstances for using a gas detector according to the invention. The field-of-view of the image capturing unit 10 comprises a background scene 100 and a free space which is filled with atmospheric gas between this background scene 100 and the image capturing unit 10. The background scene 100 may be made up of various scene elements, such as residential buildings 101, industrial buildings 102, a chimney 103, vegetation elements 104, etc. A methane pipeline 111 passes through the free space and may have a leak at a location in this pipeline. This leak causes a methane plume 110 which is therefore situated in front of some of the background scene elements 100. The goal of the invention is to reveal the existence of the methane plume 110 by providing a digital evaluation of a quantity of methane which is present between the image capturing unit 10 and the background scene 100. (i, j) designates an image point by the line and column coordinates thereof such as identified by the image sensor 2. This image point, due to its individual detection surface area—or pixel size—and the imaging relationship which is produced by each optical channel 10a, 10b, ... of the image capturing unit 10 between the field-of-view and the image sensor 2, delimits a part of the field-of-view.

The processing of the spectral images which is performed by the unit 20 is now explained.

For each spectral band in which the atmospheric composition can be considered as transparent if it does not contain target gas, the luminance at the image point (i, j) of the corresponding spectral image is approximately, for example for the band band_1:

$$L_{band\_1}(i, j) = L_{background\_1}(i, j) \cdot \tau_{band\_1} + \varepsilon_{band\_1} \cdot B(T_{ambient})$$

where $\tau_{band\_1}$ is the radiation transmission coefficient of the target gas for the spectral band concerned, i.e. band_1, effective at the image point (i, j), $\varepsilon_{band\_1}$ is the emissivity coefficient of the target gas for this same spectral band, effective at the image point (i, j), $L_{background\_1}(i, j)$ is the luminance of the background scene element at the image point (i, j) for the same spectral band, and $B(T_{ambient})$ is the Planck emission law. In this expression for the luminance which is captured in the spectral image by the image capturing unit 10 for the spectral band_1, the first term is the contribution of the background 100 through the target gas plume 110, and the second term is the contribution of the target gas plume 110. For the target gas:

$$\varepsilon_{band\_1} = 1 - \tau_{band\_1}. \text{ Then:}$$

$$L_{band\_1}(i, j) = L_{background\_1}(i, j) \cdot \tau_{band\_1} + (1 - \tau_{band\_1}) \cdot B(T_{ambient}),$$

or else:

$$L_{band\_1}(i, j) - L_{background\_1}(i, j) = L_{background\_1}(i, j) \cdot (\tau_{band\_1} - 1) + (1 - \tau_{band\_1}) \cdot B(T_{ambient}),$$

or even:

$$\tau_{band\_1} = 1 + [L_{band\_1}(i, j) - L_{background\_1}(i, j)] / [L_{background\_1}(i, j) - B(T_{ambient})].$$

By converting the luminance values into brightness temperature values, according to an affine relation which is the reciprocal of the Planck emission law inside an interval of luminance values and/or brightness temperature values which contains the values used, the following results:

$$\tau_{band\_1} = 1 + [TB_{apparent\_1}(i, j) - TB_{background\_1}(i, j)] / [TB_{background\_1}(i, j) - T_{ambient}],$$

where $TB_{apparent\_1}(i, j)$ is the apparent brightness temperature value at the image point (i, j) in the spectral image captured for the analysis band band_1, $TB_{background\_1}(i, j)$ is the background brightness temperature value as provided by the acquisition means 22 and $T_{ambient}$ is the ambient temperature value as provided by the acquisition means 21. The same ambient temperature value is used for all the spectral bands. Separately for each spectral image which is captured in an analysis band k, i.e. one of the spectral bands which is used for detecting the presence of the target gas, the image processing unit 20 thus converts the luminance value $L_{band\_k}(i, j)$ into brightness temperature value $TB_{apparent\_k}(i, j)$, and then calculates the transmission coefficient value $\tau_{band\_k}$ which is attributable to the target gas for the image point (i, j). Actually, it refers to $\tau_{band\_k}(i, j)$.

Optionally but advantageously, it is possible to get numeral values which are more exact for the target gas detection results by correcting the luminance values as provided by the image capturing unit 10, for effects of a quantity of water vapor which is contained in the atmospheric composition between the methane plume 110 and the image capturing unit 10. Indeed, for each spectral band, this quantity of water vapor produces an additional contribution to the luminance such as captured by the image sensor 2, and attenuates the contributions of the background 100 and of the target gas according to the value of a radiation transmission spectral coefficient which relates to this water vapor quantity. For this purpose, values of the spectral luminance and the spectral transmission coefficient may be calculated for water vapor, based on atmospheric data obtained elsewhere such as atmospheric pressure, relative humidity level and ambient temperature. These luminance and transmission coefficient values relating to the water vapor are $\tau_{H2O\ band\_1}$ and $L_{H2O\ band\_1}$ for the spectral band band_1, . . . , $\tau_{H2O\ band\_4}$ and $L_{H2O\ band\_4}$ for the spectral band band_4. The correction may then consist in replacing each luminance value $L_{band\_1}(i, j)$ as delivered by the image capturing unit 10, by $[L_{band\_1}(i, j) - L_{H2O\ band\_1}]/\tau_{H2O\ band\_1}$ for calculating the transmission coefficient for the target gas $\tau_{band\_1}$, and likewise for each of the other spectral bands. The same correction may be applied to the background brightness values $L_{background\_1}(i, j), \ldots, L_{background\_4}(i, j)$ when they are used for determining the background brightness temperature values $TB_{background\_1}(i, j), \ldots, TB_{background\_4}(i, j)$.

A first validation criterion for the transmission coefficient values $\tau_{band\_1}, \ldots, \tau_{band\_4}$ which are outputted by the image processing unit 20, may be that each of these values is comprised between 0 and 1, these limits 0 and 1 being allowed. Values of $\tau_{band\_1}, \ldots, \tau_{band\_4}$ which do not satisfy this criterion may be set aside, and the detection process may be resumed from the capture of the spectral images. A value close to 0 is expected for the transmission coefficient of one of the spectral bands if the target gas and/or an element of the atmospheric composition whose effects on the luminance values have not been corrected is very absorbing in this spectral band. Conversely, a value close to 1 is expected for a spectral band in which the target gas is weekly absorbing, and if there is no element in the atmospheric composition which is absorbing in this spectral band and for which the effects on the luminance values have not been corrected.

A second validation criterion for the values of the transmission coefficients $\tau_{band\_1}, \ldots, \tau_{band\_4}$, which are outputted by the image processing unit 20, may be that these numeral values are ordered according to a ranking of spectral absorption coefficient values for the target gas, which are effective one by one for the spectral bands in which the target gas is more absorbing than the atmospheric composition.

Now the operation of the calculation unit 30 is explained.

According to a first possibility, the gas detector may be adapted for deducing a numeral result for evaluating the quantity of target gas separately for each analysis band, and this for several analysis bands which are processed in parallel. The apparent brilliance temperature values have been determined independently for all the analysis bands, based on respective spectral images which were captured for these analysis bands. The image processing unit 20 has deduced from this the evaluations of the radiation transmission coefficients which relate one-to-one to these analysis bands, for all the analysis bands independently from each other. Then, the calculation unit 30 may be adapted for deducing evaluations of the quantity of the target gas $Q_{target\_gas}$ which is present in the part of the field-of-view, for example at the image point (i, j): $Q_{target\_gas}(i, j)$, also independently for each of the analysis bands, and based only on the value which was obtained for the radiation transmission coefficient relating to this analysis band. In other words, the quantity of target gas may be completely and separately evaluated based on each of the analysis bands, by using the same method but transposed to each analysis band. Then, a presence of the target gas in the field-of-view may be affirmed, denied, or declared indeterminate, based on a consistency criterion applied to the values which were obtained from all the analysis bands for the target gas quantity contained in the part of the field-of-view. Furthermore, a more reliable value for the quantity of target gas which is present at an image point may be calculated, for example, as an average of the values which were obtained separately for several analysis bands, or for all the analysis bands, for the quantity of target gas which is present at this image point.

However, another possibility for operation of the calculation unit 30, which is now described and which is preferred, may use a best-match selection algorithm.

As it is known, the value of the transmission coefficient for each spectral band results from the integral of a factor of the type $\exp[-A_{target\ gas} \cdot C_{target\ gas} - \Sigma_{other\ gas} A_{other\ gas} \cdot C_{other\ gas}]$ over a radiation path which arrives at a spectral image point (i, j), where $C_{target\ gas}$ is the local concentration of the target gas at each point of the radiation path, $A_{target\ gas}$ is the absorbance of the target gas in the spectral band considered, $C_{other\ gas}$ is a local concentration of each other gas present in the radiation path, mainly gases of the atmospheric composition for which the effects on the captured luminance values have not been corrected, and $A_{other\ gas}$ is the absorbance of this other gas in the spectral band considered. Thus, one of the spectral bands becomes more appropriate for evaluating the quantity of the target gas when the absorbance value of the target gas is larger or much larger than that of each other gas for the spectral band under consideration. Such appropriate spectral band has been called analysis band throughout the present description. Preferably, the spectral bands for the optical channels of the image capturing unit 10 were selected so that at least two of them, for example band_1 and band_2 are analysis bands for the target gas, i.e. methane in the present example. By principle, the analysis bands may not be used for determining the ambient temperature $T_{ambient}$, nor serve as reference band.

According to a preferred configuration of the calculation unit 30, it may be in data communication with the storage unit 40, and a table was initially recorded therein, which contains precalculated values for the transmission coefficients of each analysis band: $\tau_{band\_1}$ and $\tau_{band\_2}$ in the present example. These values were calculated for variable concentration profiles of the target gas along a radiation path, corresponding to variable local dilutions of the target gas in the atmospheric composition. The spectral absorbance values $A_{target\ gas}$ and $A_{other\ gas}$ which are used for these calculations were determined by spectroscopic evaluation methods, also known to the person skilled in the art. Then, for each image point (i, j) which is common to at least two spectral images of analysis bands, the calculation unit 30 selects the one of the concentration profiles of the target gas along the radiation path, for which the precalculated values of the transmission coefficients for these analysis bands best match, numerically, the values provided by the image processing unit 20 for these same transmission coefficients. An additional validation criterion for the detection of the target gas may be that one same concentration profile of the target gas along the radiation path allows accounting simultaneously with sufficient accuracy for the values of the transmission coefficients which were deduced from the spectral images for several analysis bands.

Once the concentration profile of the target gas along the radiation path which arrives at the image point (i, j) has been determined, the calculation unit 30 deduces therefrom a value of the target gas quantity $Q_{target\ gas}$ which is present on this radiation path. Possibly, for each concentration profile of the target gas, the result of the quantity of the target gas which is present on the radiation path could also have been pre-calculated, and recorded in the storage unit 40 with the values of the radiation transmission coefficients which correspond to this concentration profile for the analysis bands. Possibly, this quantity could be integrated over all the image points for which non-zero concentration points were determined, in order to evaluate the plume 110 in its entirety, inside the field-of-view.

It is understood that the invention may be reproduced by changing or adapting some secondary aspects of the embodiments which were described in detail above, while retaining at least some of the stated advantages. In particular, the following adaptations are possible:

- the spectral bands may be selected for detecting a gas other than methane, for example in order to detect quantities of hydrogen sulfide ($H_2S$), in particular such as may be produced by algae decomposing on a beach, or even for detecting a chemical-industry gas that accidentally escaped;
- the equations and formulas that have been cited, in particular for calculating the radiation transmission coefficient for each analysis band, or for correcting the effects of water vapor contained in the atmospheric composition on the luminance values captured, or for deducing the quantity of the target gas based on each radiation transmission coefficient relating to an analysis band, may be replaced by equivalent or substantially equivalent equations or formulas;
- the luminance values which are used for deducing the values of the transmission coefficients of the target gas for the analysis bands, may each be determined for a part of the field-of-view of the image capturing unit, which corresponds to several adjacent image points in spectral images instead of each relating to a single image point;
- the luminance values which are used by the imaging processing unit to get transmission coefficient values may be corrected for effects of atmospheric compounds other than water vapor, for example effects of carbon dioxide, depending on the spectral bands and the atmospheric composition on the site where the gas detector is used; and
- all numerical values which were cited were only provided for illustration purpose, and may be changed depending on the application considered.

The invention claimed is:

1. A gas detector for revealing at least one gas, called a target gas, which could be present in a field-of-view, wherein said gas detector comprises:

an image capturing unit which comprises at least two optical channels arranged in parallel for separately and simultaneously capturing respective images of one and same content of the field-of-view, called spectral images, in different spectral bands to which said at least two optical channels are dedicated one-to-one;

first acquisition means adapted for providing an ambient temperature value intended to be attributed to a quantity of the target gas which is present in the field-of-view between a background scene and the image capturing unit;

second acquisition means adapted for providing, for at least one spectral band of the different spectral bands, called at least one analysis band, background brightness temperature values which are intended to be attributed to elements of the background scene;

an image processing unit arranged for receiving the spectral images captured by the at least two optical channels of the image capturing unit and adapted for deducing, separately for each analysis band of the at least one analysis band, an evaluation of a radiation transmission coefficient which relates to said analysis band, and which is attributed at least partially to a quantity of the target gas present in a part of the field-of-view between the background scene elements and the image capturing unit, based on an equation which combines:

the ambient temperature value;

the background brightness temperature values which are intended to be attributed to the background scene elements in the part of the field-of-view, for said analysis band; and at least one brightness temperature value, called at least one apparent brightness temperature value, which corresponds to the spectral image captured for the analysis band, in said part of the field-of-view; and a calculation unit adapted for deducing an evaluation of the quantity of the target gas which is present in the part of the field-of-view based on a value of the radiation transmission coefficient which relates to an analysis band of the at least one analysis band, wherein the first acquisition means are adapted for providing the ambient temperature value according to one of the following ways:

based on at least one part of a spectral image which was captured by one of the at least two optical channels of the image capturing unit, said at least one part of the spectral image corresponding to a sector of the field-of-view declared or considered as being free of the background scene elements; and based on at least one part of a spectral image which was captured by one of the at least two optical channels of the image capturing unit whose associated spectral band is contained in a spectral domain of complete opacity for a gas which is present in a sector of the field-of-view corresponding to the at least one part of the spectral image;

wherein the gas detector is adapted for capturing the spectral image at least a part of which is used in order to provide the ambient temperature value at a same time or during a same image capturing sequence as the spectral image of each analysis band of the at least one analysis band, wherein the image processing unit then combines said ambient temperature value with said at least one brightness temperature value of said spectral image of each analysis band of the at least one analysis band;

and wherein the first acquisition means, the second acquisition means, the image processing unit and the calculation unit are implemented by at least one processor.

2. The gas detector of claim 1, wherein the image processing unit is adapted for evaluating, for each analysis band of the at least one analysis band, the radiation transmission coefficient which relates to the analysis band and which is attributed at least partially to the target gas, according to the equation:

$$\tau_{band\_1} = 1 + (TB_{apparent\_1} - TB_{background\_1})/(TB_{background\_1} - T_{ambient})$$

where:

$\tau_{band\_1}$ is the value of the radiation transmission coefficient which relates to the analysis band, indicated by band_1, and which is attributed at least partially to the target gas present in the part of the field-of-view;

$T_{ambient}$ is the ambient temperature value which is provided by the first acquisition means;

$TB_{background\_1}$ is a value of the background brightness temperature values, which are provided by the second acquisition means and which are intended to be attributed to the background scene elements contained in the part of the field-of-view, for the analysis band band_1; and $TB_{apparent\_1}$ is the at least one apparent brightness temperature value, which corresponds to the spectral image captured for the analysis band band_1, in the part of the field-of-view.

3. The gas detector of claim 1, wherein the image processing unit is further adapted for applying to each spectral image of the spectral images a correction of luminance values as captured by the image capturing unit in order to take into account at least one atmospheric compound which is present in the field-of-view, and for using the corrected luminance values for deducing the evaluation of the radiation transmission coefficient relative to each analysis band of the at least one analysis band.

4. The gas detector of claim 1, wherein the calculation unit is arranged for determining the quantity of target gas which is present in the part of the field-of-view by comparing values of the radiation transmission coefficients which were deduced by the image processing unit separately for multiple analysis bands of the at least one analysis band with values of said radiation transmission coefficients predetermined for the same multiple analysis bands recorded in a data storage unit accessible to the calculation unit, wherein said predetermined and recorded values of said radiation transmission coefficients relate to variable profiles of a concentration of the target gas on a radiation path which connects a background scene element to the image capturing unit.

5. The gas detector of claim 1, wherein the second acquisition means are adapted for providing, for each analysis band of the at least one analysis band, the background brightness temperature values according to one of the following ways:

from at least one spectral image which contains one background scene element of the background scene elements, which was captured by the optical channel of the image capturing unit dedicated to the analysis band, and which is declared or considered as having been captured when the field-of-view did not contain the target gas;

from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a transparency greater than in each analysis band of the at least one analysis band, wherein the image processing unit is adapted for identifying a material of the one background scene element from said at least one spectral image captured for the reference band and for deducing the background brightness temperature values for the analysis band and for said one background scene element based on the ambient temperature value and a spectral emissivity value of the identified material for said one background scene element; and from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a greater transparency than in each analysis band of the at least one analysis band, wherein the image processing unit is adapted for producing the background brightness temperature values for the analysis band by using a linear regression based on a background brightness temperature value deduced from the at least one spectral image captured for the reference band.

6. The gas detector of claim 5, wherein the second acquisition means are further adapted for providing, for each analysis band of the at least one analysis band, the background brightness temperature values based on the at least one spectral image captured by the one of the at least two optical channels of the image capturing unit for which the corresponding spectral band, called the reference band, is contained in the spectral domain of transparency of the target gas or in which the target gas has a greater transparency than in each analysis band of the at least one analysis band, and wherein the gas detector is adapted for capturing the at least one spectral image which corresponds to the reference band at the same time or during the same image capturing sequence as the spectral image for each analysis band of the at least one analysis band.

7. The gas detector of claim 1 wherein the image capturing unit comprises a matrix image sensor which is common to all optical channels of the at least two channels, and which is simultaneously sensitive in all of the different spectral bands of said at least two optical channels, with a part of a photosensitive surface of said matrix image sensor that is dedicated to each optical channel of the at least two optical channels separately from each other optical channel of the at least two optical channels, and each optical channel of the at least two optical channels comprising:

an optical part which is arranged in order to form an image of content of the field-of-view on the part of the photosensitive surface dedicated to said optical channel, wherein the field-of-view is common to all optical channels of the at least two optical channels; and spectral filtering means which are adapted for determining the spectral band of said optical channel.

8. The gas detector of claim 1, wherein each optical channel of the at least two optical channels of the image capturing unit comprises spectral filtering means such that the spectral band of each optical channel of said at least two optical channels has a width which is included between 10 nm and 500 nm, in terms of wavelength of radiation.

9. The gas detector of claim 8, wherein the spectral filtering means are adapted so that the different spectral bands of the at least two optical channels are contained in a first spectral domain which corresponds to radiation wavelengths comprised between 7 μm and 10 μm, or contained in a second spectral domain which corresponds to radiation wavelengths comprised between 3 μm and 5 μm.

10. The gas detector of claim 9, wherein the gas detector is adapted for methane as the target gas, and wherein:

the spectral band of a first optical channel of the at least two optical channels extends around 7.7 μm, with a spectral bandwidth which is less than 0.35 μm; and the spectral band of a second optical channel of the at least two optical channels extends around 8.05 μm, with a spectral bandwidth which is less than 0.35 μm.

11. The gas detector of claim 9, wherein the gas detector is adapted for methane as the target gas, and wherein:
the spectral band of a first optical channel of the at least two optical channels extends around 3.375 µm, with a spectral bandwidth which is less than 0.30 µm; and
the spectral band of a second optical channel of the at least two optical channels extends around 3.225 µm, with a spectral bandwidth which is less than 0.30 µ.

12. The gas detector of claim 1, wherein the gas detector is adapted for combining spectral images of the content of the field-of-view which are captured separately by two optical channels of the at least two optical channels of the image capturing unit, called base optical channels, in order to get a spectral image which corresponds to a spectral band of a composite optical channel, wherein the spectral band of the composite optical channel results from relative positions and spectral bandwidths of the respective spectral bands of the two base optical channels.

13. The gas detector of claim 1, wherein the gas detector is adapted for revealing several different target gases which could be simultaneously present in the field-of-view; and wherein the spectral band of at least one optical channel of the at least two optical channels of the image capturing unit is simultaneously contained in respective spectral absorption domains of at least two target gases of the several different target gases so that one same spectral image which is captured by said at least one optical channel is used by the image processing unit and the calculation unit for deducing evaluations of respective quantities of said at least two target gases which are present in the field-of-view.

14. The gas detector of claim 10, wherein:
the spectral band of a third optical channel of the at least two optical channels extends around 7.35 µm, with a spectral bandwidth which is less than 0.35 µm; and
the spectral band of a fourth optical channel of the at least two optical channels extends around 8.35 µm or 9.05 µm, with a spectral bandwidth which is less than 0.35 µm.

15. The gas detector of claim 11, wherein:
the spectral band of a third optical channel of the at least two optical channels extends around 3.05 µm, with a spectral bandwidth which is less than 0.30 µm; and
the spectral band of a fourth optical channel of the at least two optical channels extends around 4.237 µm or 3.505 µm, with a spectral bandwidth which is less than 0.30 µm.

16. The gas detector of claim 2, wherein the image processing unit is further adapted for applying to each spectral image of the spectral images a correction of luminance values as captured by the image capturing unit in order to take into account at least one atmospheric compound which is present in the field-of-view, and for using the corrected luminance values for deducing the evaluation of the radiation transmission coefficient relative to each analysis band of the at least one analysis band.

17. The gas detector of claim 2, wherein the calculation unit is arranged for determining the quantity of target gas which is present in the part of the field-of-view by comparing values of the radiation transmission coefficients which were deduced by the image processing unit separately for multiple analysis bands of the at least one analysis band with values of said radiation transmission coefficients predetermined for the same multiple analysis bands recorded in a data storage unit accessible to the calculation unit, wherein said predetermined and recorded values of said radiation transmission coefficients relate to variable profiles of a concentration of the target gas on a radiation path which connects a background scene element to the image capturing unit.

18. The gas detector of claim 3, wherein the calculation unit is arranged for determining the quantity of target gas which is present in the part of the field-of-view by comparing values of the radiation transmission coefficients which were deduced by the image processing unit separately for multiple analysis bands of the at least one analysis band with values of said radiation transmission coefficients predetermined for the same multiple analysis bands recorded in a data storage unit accessible to the calculation unit, wherein said predetermined and recorded values of said radiation transmission coefficients relate to variable profiles of a concentration of the target gas on a radiation path which connects a background scene element to the image capturing unit.

19. The gas detector of claim 2, wherein the second acquisition means are adapted for providing, for each analysis band of the at least one analysis band, the background brightness temperature values according to one of the following ways:
from at least one spectral image which contains one background scene element of the background scene elements, which was captured by the optical channel of the image capturing unit dedicated to the analysis band, and which is declared or considered as having been captured when the field-of-view did not contain the target gas;
from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a transparency greater than in each analysis band of the at least one analysis band, wherein the image processing unit is adapted for identifying a material of the one background scene element from said at least one spectral image captured for the reference band and for deducing the background brightness temperature values for the analysis band and for said one background scene element based on the ambient temperature value and a spectral emissivity value of the identified material for said one background scene element; and
from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a greater transparency than in each analysis band of the at least one analysis band, wherein the image processing unit is adapted for producing the background brightness temperature values for the analysis band by using a linear regression based on a background brightness temperature value deduced from the at least one spectral image captured for the reference band.

20. The gas detector of claim 3, wherein the second acquisition means are adapted for providing, for each analysis band of the at least one analysis band, the background brightness temperature values according to one of the following ways:
from at least one spectral image which contains one background scene element of the background scene elements, which was captured by the optical channel of the image capturing unit dedicated to the analysis band, and which is declared or considered as having been captured when the field-of-view did not contain the target gas;

from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a transparency greater than in each analysis band of the at least one analysis band, wherein the image processing unit is adapted for identifying a material of the one background scene element from said at least one spectral image captured for the reference band and for deducing the background brightness temperature values for the analysis band and for said one background scene element based on the ambient temperature value and a spectral emissivity value of the identified material for said one background scene element; and from at least one spectral image which contains one background scene element of the background scene elements and which was captured by one of the at least two optical channels of the image capturing unit for which the corresponding spectral band, called reference band, is contained in a spectral domain of transparency of the target gas or in which the target gas has a greater transparency than in each analysis band of the at least one analysis band, wherein the image processing unit is adapted for producing the background brightness temperature values for the analysis band by using a linear regression based on a background brightness temperature value deduced from the at least one spectral image captured for the reference band.

* * * * *